(12) United States Patent
Augustine et al.

(10) Patent No.: US 7,714,255 B2
(45) Date of Patent: May 11, 2010

(54) BUS BAR ATTACHMENTS FOR FLEXIBLE HEATING ELEMENTS

(75) Inventors: Scott D. Augustine, Bloomington, MN (US); Randall C. Arnold, Minnetonka, MN (US); Keith J. Leland, Medina, MN (US)

(73) Assignee: Augustine BioMedical and Design, LLC, Eden Prairie, MN (US)

( * ) Notice: Subject to any disclaimer, the term of this patent is extended or adjusted under 35 U.S.C. 154(b) by 184 days.

(21) Appl. No.: 11/537,212

(22) Filed: Sep. 29, 2006

(65) Prior Publication Data
US 2007/0068923 A1    Mar. 29, 2007

Related U.S. Application Data

(60) Provisional application No. 60/825,573, filed on Sep. 13, 2006, provisional application No. 60/722,106, filed on Sep. 29, 2005, provisional application No. 60/722,246, filed on Sep. 29, 2005.

(51) Int. Cl.
  H05B 1/00    (2006.01)
  H05B 3/00    (2006.01)
(52) U.S. Cl. ...................... 219/212; 219/200
(58) Field of Classification Search ........... 219/211, 219/212, 217, 528, 529, 543, 542, 545, 549, 219/527, 209, 544, 548; 392/435, 432, 425
See application file for complete search history.

(56) References Cited

U.S. PATENT DOCUMENTS

| | | | |
|---|---|---|---|
| 3,808,403 A | 4/1974 | Kanaya et al. | |
| 3,839,621 A | 10/1974 | Hariu | |
| 3,900,654 A | 8/1975 | Stinger | |
| 3,936,661 A | 2/1976 | Furuishi et al. | |
| 4,061,898 A | 12/1977 | Murray et al. | |
| 4,149,066 A | 4/1979 | Niibe | |
| 4,479,795 A | 10/1984 | Mustacich et al. | |
| 4,534,886 A | 8/1985 | Kraus et al. | |
| 4,626,664 A | 12/1986 | Grise | |
| 4,719,335 A | 1/1988 | Batliwalla et al. | |

(Continued)

FOREIGN PATENT DOCUMENTS

GB            586745          3/1947

(Continued)

OTHER PUBLICATIONS

EeonTexTM Conductive Textiles, Product Details, www.eeonyx.com/prodte.html, Sep. 19, 2006, pp. 1-5.

(Continued)

Primary Examiner—Daniel L Robinson
(74) Attorney, Agent, or Firm—Fredrikson & Byron, P.A.

(57) ABSTRACT

A flexible heating subassembly, that may be incorporated in a heating blanket or any other type of flexible heater, includes a flexible sheet-like heating element, or heater, to which first and second conductive bus bars are coupled, each with a respective first and second row of conductive stitching. A first electrically insulating member is interposed between the first bus bar and the heater and is secured therebetween by the first row of stitching, and a second electrically insulating member is interposed between the second bus bar and the heater and is secured therebetween by the second row of stitching. The first and second insulating members prevent direct electrical contact between respective first and second bus bars and the heater.

39 Claims, 12 Drawing Sheets

U.S. PATENT DOCUMENTS

| | | | |
|---|---|---|---|
| 4,764,665 A | 8/1988 | Orban et al. | |
| 4,798,936 A | 1/1989 | Johnson, Sr. | |
| 4,912,306 A | 3/1990 | Grise et al. | |
| 5,008,515 A | 4/1991 | McCormack | |
| 5,010,233 A * | 4/1991 | Henschen et al. | 219/209 |
| 5,023,433 A | 6/1991 | Gordon | |
| 5,380,580 A | 1/1995 | Rogers et al. | |
| 5,422,462 A | 6/1995 | Kishimoto | |
| 5,443,056 A | 8/1995 | Smith et al. | |
| 5,773,275 A | 6/1998 | Anderson et al. | |
| 5,817,145 A | 10/1998 | Augustine et al. | |
| 5,824,996 A | 10/1998 | Kochman et al. | |
| 5,928,274 A | 7/1999 | Augustine | |
| 5,964,792 A | 10/1999 | Augustine | |
| 5,974,605 A | 11/1999 | Dickerhoff et al. | |
| 5,986,243 A | 11/1999 | Campf | |
| 6,078,026 A | 6/2000 | West | |
| 6,093,910 A | 7/2000 | McClintock et al. | |
| 6,172,344 B1 * | 1/2001 | Gordon et al. | 219/529 |
| 6,184,496 B1 | 2/2001 | Pearce | |
| 6,235,049 B1 | 5/2001 | Nazerian | |
| 6,373,034 B1 | 4/2002 | Rock et al. | |
| 6,403,935 B2 | 6/2002 | Kochman et al. | |
| 6,483,087 B2 | 11/2002 | Gardner et al. | |
| 6,582,456 B1 | 6/2003 | Hand et al. | |
| 6,770,848 B2 | 8/2004 | Haas et al. | |
| 6,770,854 B1 | 8/2004 | Keane | |
| 6,839,922 B1 | 1/2005 | Foggett et al. | |
| 6,933,469 B2 | 8/2005 | Ellis et al. | |
| 6,974,935 B2 | 12/2005 | O'Grady | |
| 7,022,950 B2 | 4/2006 | Haas et al. | |
| 7,053,344 B1 * | 5/2006 | Surjan et al. | 219/549 |
| 2002/0005398 A1 | 1/2002 | Gillner et al. | |
| 2002/0117495 A1 | 8/2002 | Kochman et al. | |
| 2005/0016982 A1 | 1/2005 | Campf et al. | |

OTHER PUBLICATIONS

U.S. Appl. No. 11/537,173, Office Action dated Mar. 26, 2007, 8 pages.
U.S. Appl. No. 11/537,173, Office Action dated Oct. 17, 2007, 8 pages.
U.S. Appl. No. 11/537,173, Office Action dated Apr. 30, 2008, 9 pages.
U.S. Appl. No. 11/537,179, Office Action dated Aug. 16, 2007, 6 pages.
U.S. Appl. No. 11/537,179, Office Action dated Dec. 31, 2007, 18 pages.
U.S. Appl. No. 11/537,189, Office Action dated Aug. 16, 2007, 5 pages.
U.S. Appl. No. 11/537,189, Office Action dated Dec. 28, 2007, 12 pages.
U.S. Appl. No. 11/537,222, Office Action dated Feb. 23, 2007, 8 pages.
U.S. Appl. No. 11/537,222, Office Action dated Jul. 18, 2007, 6 pages.
U.S. Appl. No. 11/537,222, Final Office Action dated May 1, 2008, 7 pages.
PCT Application No. PCT/US2006/038232, International Search Report and Written Opinion, dated Jan. 23, 2007, 11 pages.
PCT Application No. PCT/US2006/038231, International Search Report and Written Opinion, dated Aug. 20, 2007, 8 pages.
U.S. Appl. No. 11/537,179, Office Action dated May 27, 2009, 17 pages.
U.S. Appl. No. 11/537,189, Office Action dated Apr. 28, 2009. 14 pages.
U.S. Appl. No. 11/537,222, Final Office Action, dated Nov. 12, 2008, 7 pages.
U.S. Appl. No. 11/537,173, Office Action, dated Dec. 10, 2008, 10 pages.
U.S. Appl. No. 11/537,179, Final Office Action, dated Aug. 7, 2008, 15 pages.
U.S. Appl. No. 11/537,189, Final Office Action, dated Aug. 6, 2008, 12 pages.

* cited by examiner

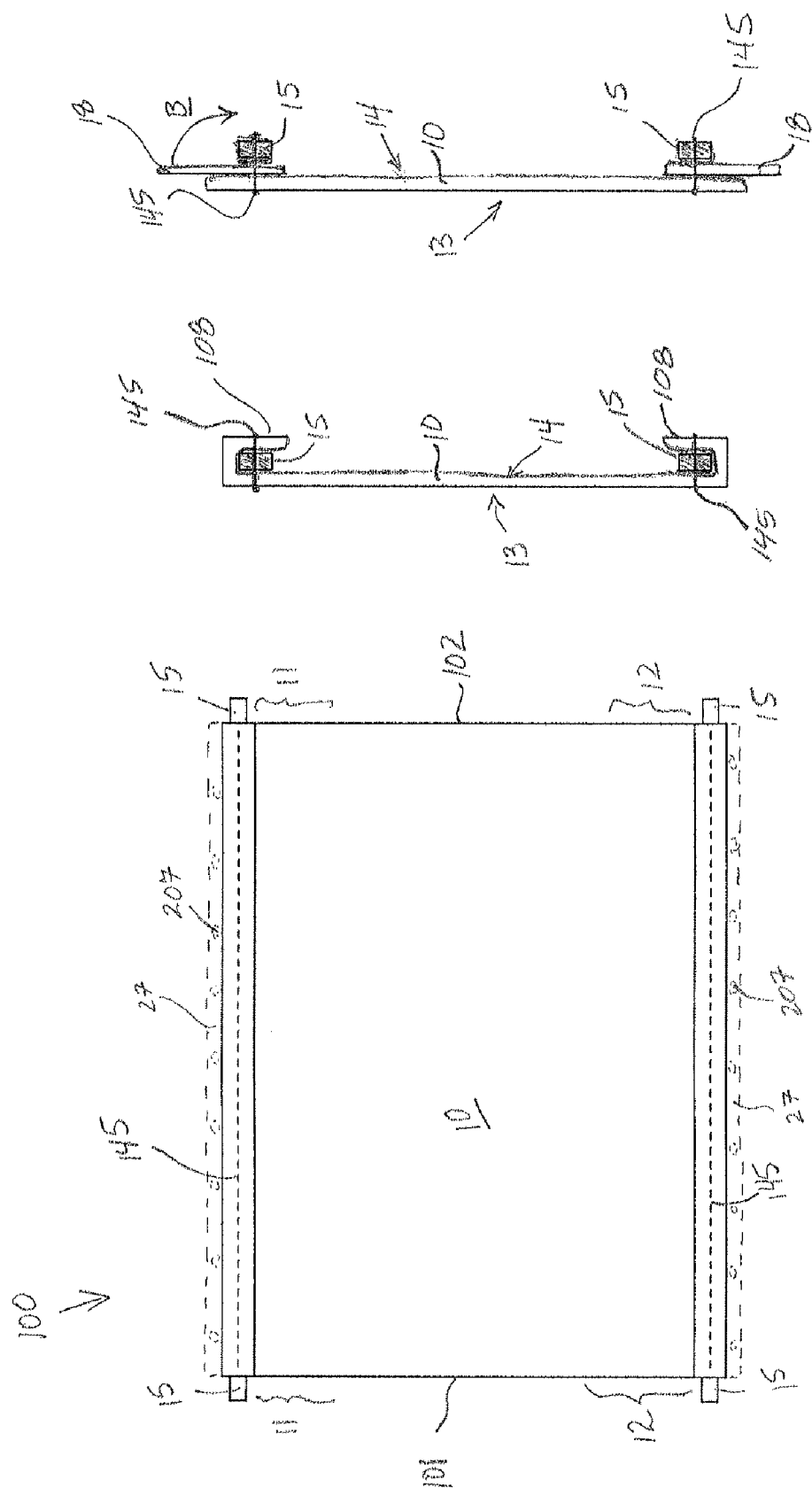

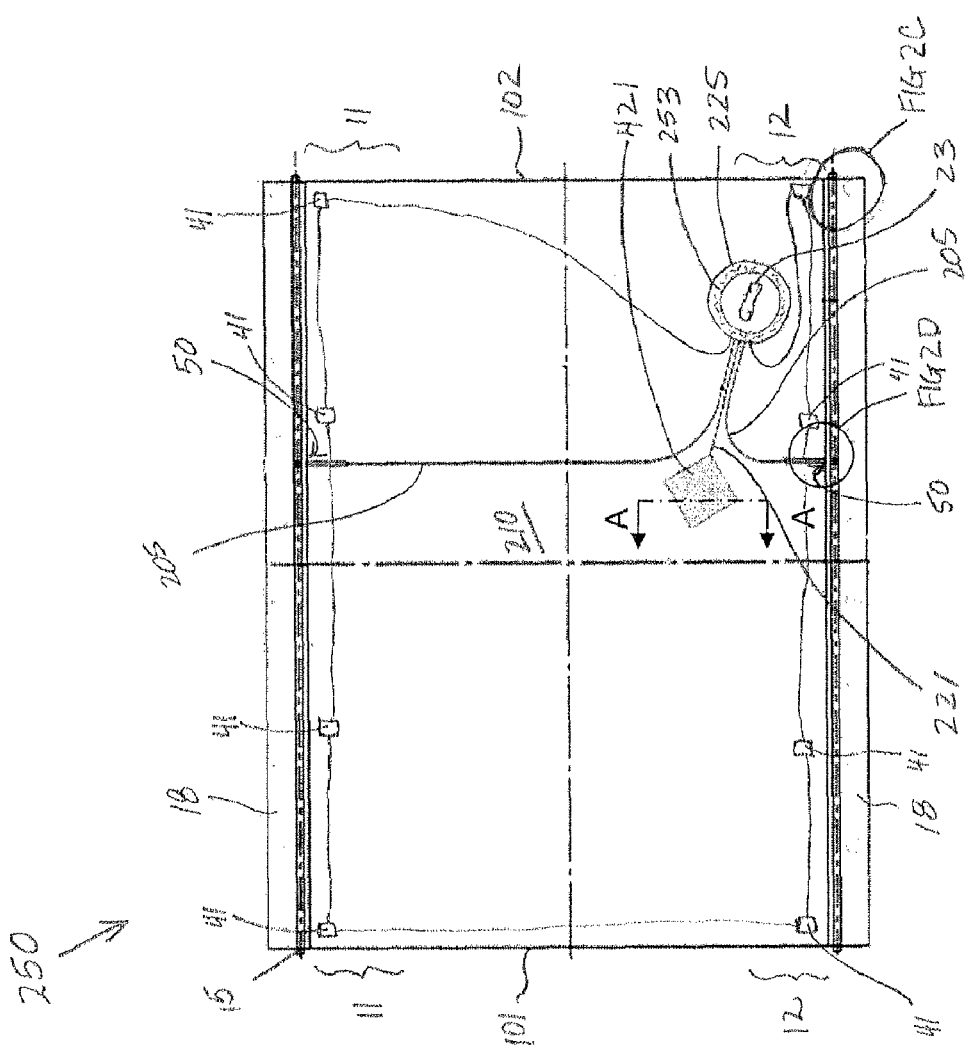
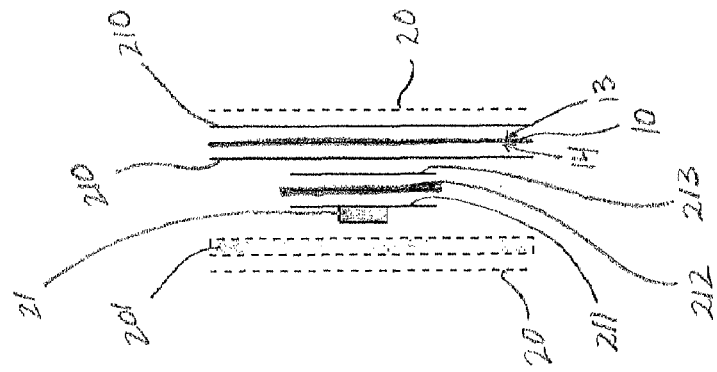
Figure 2A
Figure 2B

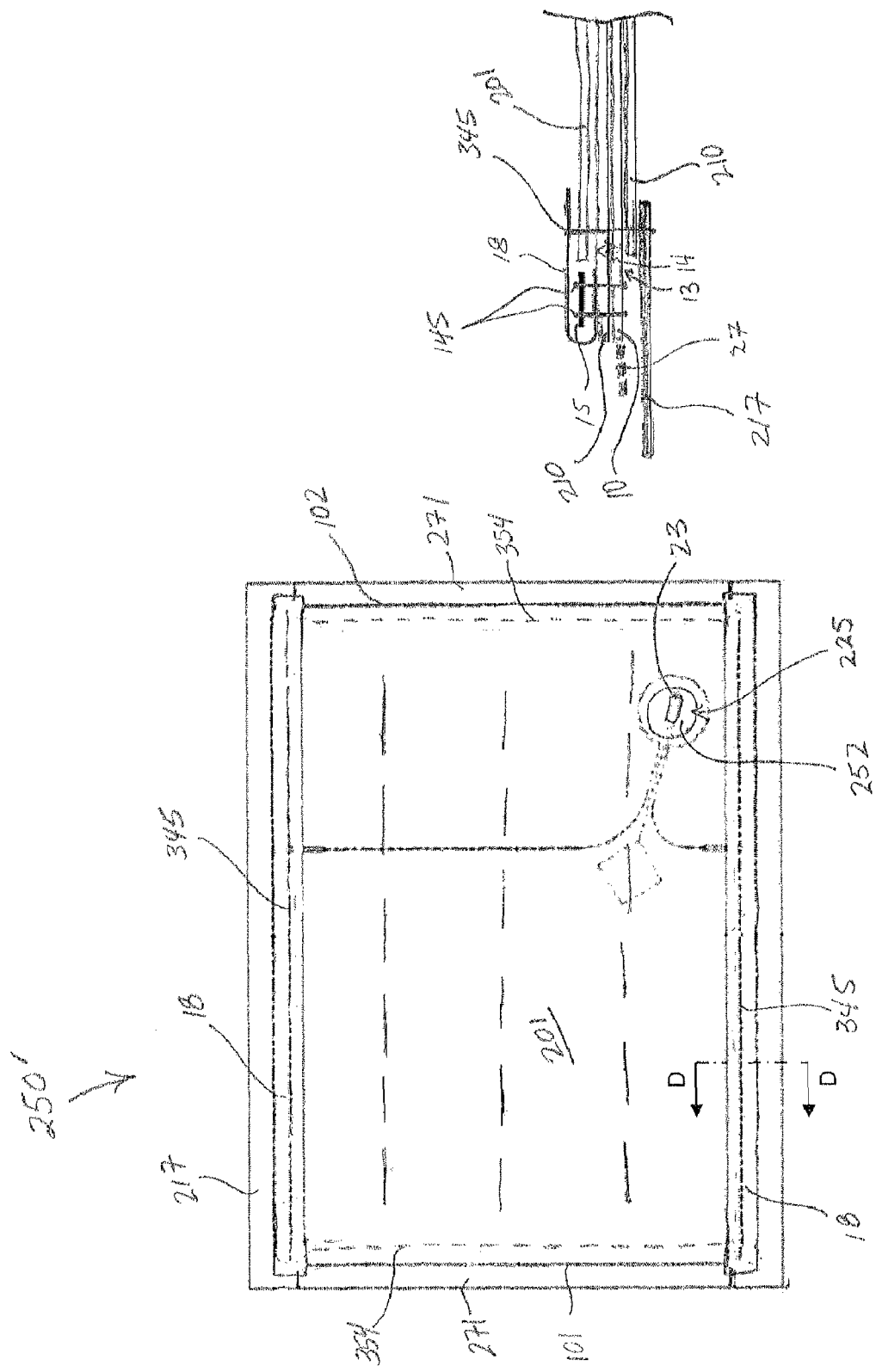

BUS BAR ATTACHMENTS FOR FLEXIBLE HEATING ELEMENTS

PRIORITY CLAIM

The present application claims priority to co-pending provisional applications Ser. No. 60/825,573, entitled HEATING BLANKET SYSTEM filed on Sep. 13, 2006; Ser. No. 60/722,106, entitled ELECTRIC WARMING BLANKET INCLUDING TEMPERATURE ZONES AUTOMATICALLY OPTIMIZED, filed Sep. 29, 2005; and Ser. No. 60/722,246, entitled HEATING BLANKET, filed Sep. 29, 2005; all of which are incorporated by reference in their entireties herein.

RELATED APPLICATIONS

The present application is related to the following commonly assigned utility patent applications, all of which are filed concurrently herewith and all of which are hereby incorporated by reference in their entireties: A) ELECTRIC WARMING BLANKET HAVING OPTIMIZED TEMPERATURE ZONES, Practitioner Ser. No. 11/537,173; B) NOVEL DESIGNS FOR HEATING BLANKETS AND PADS, Practitioner Ser. No. 11/537,179; C) TEMPERATURE SENSOR ASSEMBLIES FOR ELECTRIC WARMING BLANKETS, Practitioner Ser. No. 11/537,189; D) NOVEL DESIGNS FOR AN ELECTRIC WARMING BLANKET INCLUDING A FLEXIBLE HEATER, Practitioner Ser. No. 11/537,199; and E) BUS BAR INTERFACES FOR FLEXIBLE HEATING ELEMENTS, Practitioner Ser. No. 11/537,212.

TECHNICAL FIELD

The present invention is related to flexible sheet-like heating elements, or heaters, and more particularly to bus bar couplings for such heaters.

BACKGROUND

It is well established that surgical patients under anesthesia become poikilothermic. This means that the patients lose their ability to control their body temperature and will take on or lose heat depending on the temperature of the environment. Since modern operating rooms are all air conditioned to a relatively low temperature for surgeon comfort, the majority of patients undergoing general anesthesia will lose heat and become clinically hypothermic if not warmed.

Over the past 15 years, forced-air warming (FAW) has become the "standard of care" for preventing and treating the hypothermia caused by anesthesia and surgery. FAW consists of a large heater/blower attached by a hose to an inflatable air blanket. The warm air is distributed over the patient within the chambers of the blanket and then is exhausted onto the patient through holes in the bottom surface of the blanket.

Although FAW is clinically effective, it suffers from several problems including: a relatively high price; air blowing in the operating room, which can be noisy and can potentially contaminate the surgical field; and bulkiness, which, at times, may obscure the view of the surgeon. Moreover, the low specific heat of air and the rapid loss of heat from air require that the temperature of the air, as it leaves the hose, be dangerously high—in some products as high as 45° C. This poses significant dangers for the patient. Second and third degree burns have occurred both because of contact between the hose and the patient's skin, and by blowing hot air directly from the hose onto the skin without connecting a blanket to the hose. This condition is common enough to have its own name—"hosing." The manufacturers of forced air warming equipment actively warn their users against hosing and the risks it poses to the patient.

Electric warming blankets overcome the aforementioned problems with FAW. Some of these warming blankets employ flexible heaters, the flexibility of which is desirable to maintain when employing in the blankets. In applications such as these, where the heater is subject to flexing, couplings directly between the heater and bus bars, which extend along opposing edges of the heater to supply power to the heater, may be susceptible to zones of intermittent contact along a length of each of the bus bars. Thus there is a need for flexible heater subassemblies that include bus bar couplings which are not susceptible to zones of intermittent contact.

The standard method of coupling the electrical power supply to any large heater surface is to place a metal bus bar conductor near two of the opposing edges of the heater. Electrical power flows from the power supply through the bus bars and is evenly distributed along the entire length of the heater. The electrically conductive bus bar material contacts the electrically conductive heater and the current flows between the two materials. Unfortunately, the conductive bus bars do not make a dependable, uniform and stable connection to the conductive heater, especially during flexing of the heater, because both the heater and the bus bar are flexible. Generally, two flexible pieces of material that are placed together will not maintain reliable and uniform contact across their entire surface, especially during repeated flexing.

When the bus bar/heater interface is flexed, the heater temporarily separates slightly from the bus bar at point locations. This separation prevents current from flowing at the separation point, forcing the current that would have passed through that point to flow instead through adjacent points that are still in contact. The increased current flowing through the adjacent points can cause those points to over-heat. Repeated over-heating can cause the heater at that point to eventually fail and stop conducting electricity. When a point fails, it is permanently removed from the current path and the adjacent points must pick up the extra flow. The extra flow caused by the failed points, in addition to the extra flow caused by the areas of non-contact due to flexion, may result in over-heating and failure of the remaining points.

Accordingly, there remains a need for flexible heater subassemblies and blankets that allow the bus bar and the heater to be coupled in such a manner that current can be dependably and uniformly supplied from the bus bar to the heater without potentially patient harming blanket over-heating and/or failure. Various embodiments of the invention described herein solve one or more of the problems discussed above.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 1A is a plan view of a flexible heating blanket subassembly for a heating blanket, according to some embodiments of the present invention.

FIGS. 1B-C are end views of two embodiments of the subassembly shown in FIG. 1A.

FIG. 2A is a top plan view of a heating element assembly, according to some embodiments of the present invention, which may be incorporated in the blanket shown in FIG. 3A.

FIG. 2B is a section view through section line A-A of FIG. 2A.

FIG. 3C is a top plan view of a heating element assembly, which may be incorporated in the blanket shown in FIG. 3A.

FIG. 3D is an cross-section view through section line D-D of FIG. 3C.

DETAILED DESCRIPTION

Figure 1D:
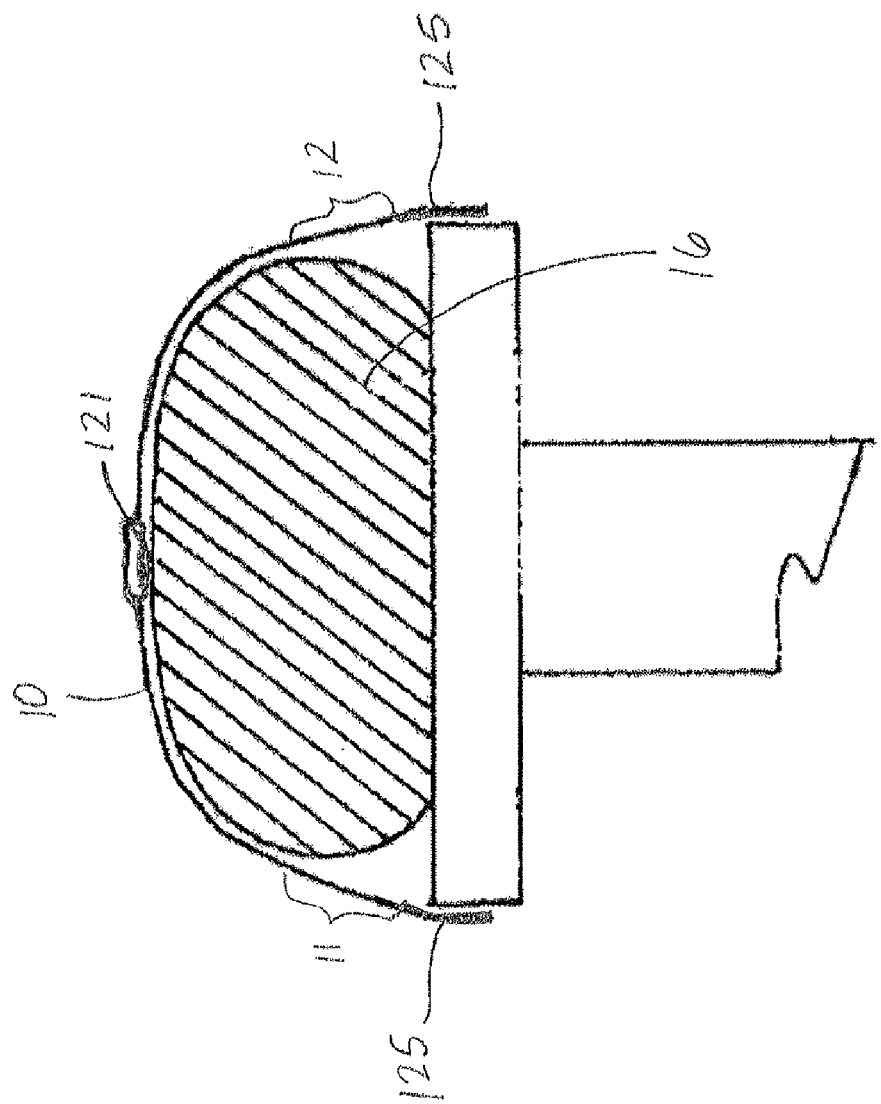
FIG. 1D is a schematic showing a blanket including the subassembly of FIG. 1A draped over a body.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized. The term 'blanket', used to describe embodiments of the present invention, may be considered to encompass heating blankets and pads.

FIG. 1A is a plan view of a flexible heating blanket subassembly 100, according to some embodiments of the present invention; and FIGS. 1B-C are end views of two embodiments of the subassembly shown in FIG. 1A. FIG. 1A illustrates a flexible sheet-like heating element or heater 10 of subassembly 100 including a first end 101, a second end 102, a first lateral portion 11 extending between ends 101, 102, and a second lateral portion 12, opposite first lateral portion 11, also extending between ends 101, 102. According to preferred embodiments of the present invention, heating element 10 comprises a conductive fabric or a fabric incorporating closely spaced conductive elements such that heating element 10 has a substantially uniform watt density output, preferably less than approximately 0.5 watts/sq. inch, and more preferably between approximately 0.2 and approximately 0.4 watts/sq. inch, across a surface area, of one or both sides 13, 14 (FIGS. 1B-C), the surface area including and extending between lateral portions 11, 12 of heating element 10. Some examples of conductive fabrics which may be employed by embodiments of the present invention include, without limitation, carbon fiber fabrics, fabrics made from carbonized fibers, woven or non-woven non-conductive substrates coated with a conductive material, for example, polypyrrole, carbonized ink, or metalized ink.

FIG. 1A further illustrates subassembly 100 including two bus bars 15 coupled to heater 10 for powering element 10; each bar 15 is shown extending alongside opposing lateral portions 11, 12, between first and second ends 101, 102. With reference to FIG. 1B, according to some embodiments, bus bars 15 are coupled to heater 10 within folds of opposing wrapped perimeter edges 108 of heater 10 by a stitched coupling 145, for example, formed with conductive thread such as silver-coated polyester or nylon thread (Marktek Inc., Chesterfield, Mo.), extending through edges 108 of heater 10, bars 15, and again through heater 10 on opposite side of bars 15. According to alternate embodiments heater 10 is not folded over bus bars 15 as shown. Alternative threads or yarns employed by embodiments of the present invention may be made of other polymeric or natural fibers coated with other electrically conductive materials; in addition, nickel, gold, platinum and various conductive polymers can be used to make conductive threads. Metal threads such as stainless steel, copper or nickel could also be used for this application. According to an exemplary embodiment, bars 15 are comprised of flattened tubes of braided wires, such as are known to those skilled in the art, for example, a flat braided silver coated copper wire, and may thus accommodate the thread extending therethrough, passing through openings between the braided wires thereof. In addition such bars are flexible to enhance the flexibility of blanket subassembly 100. According to alternate embodiments, bus bars 15 can be a conductive foil or wire, flattened braided wires not formed in tubes, an embroidery of conductive thread, or a printing of conductive ink. Preferably, bus bars 15 are each a flat braided silver-coated copper wire material, since a silver coating has shown superior durability with repeated flexion, as compared to tin-coated wire, for example, and may be less susceptible to oxidative interaction with a polypyrrole coating of heater 10 according to an embodiment described below. Additionally, an oxidative potential, related to dissimilar metals in contact with one another is reduced if a silver-coated thread is used for stitched coupling 145 of a silver-coated bus bar 15.

According to some preferred embodiments, two or more rows of stitches are applied to each bus bar 15 for added safety and stability of the bus bar/heating element interface. Preferably, the two rows of stitches are oriented in a "zigzag" pattern so that each row of stitches captures an edge of bus bar 15. A zigzag pattern of relatively closely positioned stitches stabilizes flexible heating element 10 and holds it in close opposition to bus bar 15 so that heating element 10 cannot physically pull away from bus bar 15 at the bus bar/heating element interface during flexing. According to some additional embodiments, a ribbon of highly conductive material is interposed between bus bar 15 and heater 10. For example, a ribbon of cloth that has been coated with a conductive metal such as silver works very well in this application. The cloth ribbon is soft, flexible and fibrous and therefore integrates itself into the fibrous matrix of bus bar 15, and that of heater 10, if heater 10 comprises a conductive fabric. Other options for improving the electrical connection between bus bar 15 and heater 10 include a ribbon of highly conductive paint or ink, applied to the heater 10 at the bus bar/heating element interface.

According to an exemplary embodiment, a conductive fabric comprising heating element 10 comprises a non-woven polyester having a basis weight of approximately 130 g/m² and being 100% coated with polypyrrole (available from Eeonyx Inc., Pinole, Calif.); the coated fabric has an average resistance, for example, determined with a four point probe measurement, of approximately 15-20 ohms per square inch at about 48 volts, which is suitable to produce the preferred watt density of 0.2 to 0.4 watts/sq. in. for surface areas of heating element 10 having a width, between bus bars 15, in the neighborhood of about 20 inches. Such a width is suitable for a lower body heating blanket, some embodiments of which will be described below. A resistance of such a conductive fabric may be tailored for different widths between bus bars (wider requiring a lower resistance and narrower requiring a higher resistance) by increasing or decreasing a surface area of the fabric that can receive the conductive coating, for example by increasing or decreasing the basis weight of the fabric. Resistances over surface areas of conductive fabrics such these may vary, for example, due to variation in a thickness of a conductive coating, variation within the conductive coating itself, variation in effective surface area of the substrate which is available to receive the conductive coating, or variation in the density of the substrate itself. Local surface resistance across a heating element, for example element 10, is directly related to heat generation according to the following relationship:

$$Q \text{ (Joules)} = I^2 \text{(Amps)} \times R \text{ (Ohms)}$$

Variability in resistance thus translates into variability in heat generation, which is measured as a temperature. According to preferred embodiments of the present invention, which are employed to warm patients undergoing surgery, precise temperature control is desirable. Means for determining heating element temperatures, which average out temperature variability caused by resistance variability across a surface of the heating element, are described below in conjunction with FIGS. 2A-B.

A flexibility of blanket subassembly 100, provided primarily by flexible heating element 10, and optionally enhanced by the incorporation of flexible bus bars, allows blanket subassembly 100 to conform to the contours of a body, for example, all or a portion of a patient undergoing surgery, rather than simply bridging across high spots of the body; such conformance may optimize a conductive heat transfer from element 10 to a surface of the body. However, as illustrated in FIG. 1D, heating element 10 may be draped over a body 16 such that lateral portions 11, 12 do not contact side surfaces of body 16; the mechanism of heat transfer between portions 11, 12 and body 16, as illustrated in FIG. 1D, is primarily radiant with some convection.

The uniform watt-density output across the surface areas of preferred embodiments of heating element 10 translates into generally uniform heating of the surface areas, but not necessarily a uniform temperature. At locations of heating element 10 which are in conductive contact with a body acting as a heat sink, for example, body 16, the heat is efficiently drawn away from heating element 10 and into the body, for example by blood flow, while at those locations where element 10 does not come into conductive contact with the body, for example lateral portions 11, 12 as illustrated in FIG. 1D, an insulating air gap exists between the body and those portions, so that the heat is not drawn off those portions as easily. Therefore, those portions of heating element 10 not in conductive contact with the body will gain in temperature, since heat is not transferred as efficiently from these portions as from those in conductive contact with the body. The 'non-contacting' portions will reach a higher equilibrium temperature than that of the 'contacting' portions, when the radiant and convective heat loss equal the constant heat production through heating element 10. Although radiant and convective heat transfer are more efficient at higher heater temperatures, the laws of thermodynamics dictate that as long as there is a uniform watt-density of heat production, even at the higher temperature, the radiant and convective heat transfer from a blanket of this construction will result in a lower heat flux to the skin than the heat flux caused by the conductive heat transfer at the 'contacting' portions at the lower temperature. Even though the temperature is higher, the watt-density is uniform and, since the radiant and convective heat transfer are less efficient than conductive heat transfer, the 'non-contacting' portions must have a lower heat flux. Therefore, by controlling the 'contacting' portions to a safe temperature, for example, via a temperature sensor 121 coupled to heating element 10 in a location where element 10 will be in conductive contact with the body, as illustrated in FIG. 1D, the 'non-contacting' portions, for example, lateral portions 11, 12, will also be operating at a safe temperature because of the less efficient radiant and convective heat transfer. According to preferred embodiments, heating element 10 comprises a conductive fabric having a relatively small thermal mass so that when a portion of the heater that is operating at the higher temperature is touched, suddenly converting a 'non-contacting' portion into a 'contacting' portion, that portion will cool almost instantly to the lower operating temperature.

According to embodiments of the present invention, zones of heating element 10 may be differentiated according to whether or not portions of element 10 are in conductive contact with a body, for example, a patient undergoing surgery. In the case of conductive heating, gentle external pressure may be applied to a heating blanket including heating element 10, which pressure forces heating element 10 into better conductive contact with the patient to improve heat transfer. However, if excessive pressure is applied the blood flow to that skin may be reduced at the same time that the heat transfer is improved and this combination of heat and pressure to the skin can be dangerous. It is well known that patients with poor perfusion should not have prolonged contact with conductive heat in excess of approximately 42° C. 42° C. has been shown in several studies to be the highest skin temperature, which cannot cause thermal damage to normally perfused skin, even with prolonged exposure. (Stoll & Greene, Relationship between pain and tissue damage due to thermal radiation. J. Applied Physiology 14(3):373-382. 1959. and Moritz and Henriques, Studies of thermal injury: The relative importance of time and surface temperature in the causation of cutaneous burns. Am. J. Pathology 23:695-720, 1947) Thus, according to certain embodiments of the present invention, the portion of heating element 10 that is in conductive contact with the patient is controlled to approximately 43° C. in order to achieve a temperature of about 41-42° C. on a surface a heating blanket cover that surrounds element 10, for example, a cover or shell 20, 40 which will be described below in conjunction with FIGS. 3A and 4C. With further reference to FIG. 1D, flaps 125 are shown extending laterally from either side of heating element 10 in order to enclose the sides of body 16 thereby preventing heat loss; according to preferred embodiments of the present invention, flaps 125 are not heated and thus provide no thermal injury risk to body if they were to be tucked beneath sides of body 16.

Referring now to the end view of FIG. 1C, an alternate embodiment to that shown in FIG. 1B is presented. FIG. 1C illustrates subassembly 100 wherein insulating members 18, for example, fiberglass material strips having an optional PTFE coating and a thickness of approximately 0.003 inch, extend between bus bars 15 and heating element 10 at each stitched coupling 145, so that electrical contact points between bars 15 and heating element 10 are solely defined by the conductive thread of stitched couplings 145. Alternatively, the electrical insulation material layer could be made of polymeric film, a polymeric film reinforced with a fibrous material, a cellulose material, a glass fibrous material, rubber sheeting, polymeric or rubber coated fabric or woven materials or any other suitable electrically insulating material. Each of the conductive thread stitches of coupling 145 maintains a stable and constant contact with bus bar 15 on one side and heating element 10 on the other side of insulator 18. Specifically, the stitches produce a stable contact in the face of any degree of flexion, so that the potential problem of intermittent contact between bus bar 15 and heating element 10 (that could arise for the embodiment shown in FIG. 1B, where bus bar 15 is in physical contact with heating element 10) can be avoided. The stitches are the only electrical connection between bus bar 15 and heating element 10, but, since the conductive thread has a much lower electrical resistance than that of heating element 10, the thread does not heat under normal conditions. In addition to heating blanket applications described herein, such a design for providing for a uniform and stable conductive interface between a bus bar and a heater material can be used to improve the conductive interface between a bus bar or electrode and conductive non-flexible heaters, for example, in electronic shielding, in radar shielding and in other applications.

Preferably, coupling 145 includes two or more rows of stitches for added security and stability. However, due to the flexible nature of blanket subassembly 100, the thread of stitched couplings 145, for either embodiment of FIG. 1B or FIG. 1C, may undergo stresses that, over time and with multiple uses of a blanket containing subassembly 100, could lead to one or more fractures along the length of stitching 145. Such a fracture, if it occurred in the embodiment of FIG. 1B, could also result in intermittent contact points, between bus bar 15 and heating element 10, that could lead to a melt down of element 10 along bus bar. But, if such a fracture were to occur in the embodiment of FIG. 1C, insulating member 18 may prevent a meltdown of element 10, so that only the conductive thread of stitching 145 melts down along bus bar 15.

Referring back to FIG. 1A, bus bars 15 are shown extending past ends 101 and 102 of heater 10, according to preferred embodiments. If bus bars did not extend at least to ends 101 and 102, increased current would flow from ends of bus bars 15 and into heater 10. Normally the current flows approximately perpendicularly between bus bars 15, therefore, each point on one of bus bars 15 supplies a narrow line of current to the other of bus bars 15. If either bus bar 15 terminates before reaching the end of heater 10, current will flow out the end of that bus bar. The excess current flow can result in excessive heating of an area of heater 10, adjacent the end of that bus bar, which can cause degradation of heater 10 leading to a catastrophic failure of heater 10 by spreading along the entire bus bar. To avoid such a failure and to improve manufacturing reliability, both ends of bus bars 15 are extended beyond ends 101, 102 of heater 10, preferably over a length of at least approximately ½ cm. According to these embodiments, the conductive thread stitches, previously described, also extend past ends 101, 102 being terminated on the bus bar extensions. This design advantageously creates an easy manufacturing process, which assures a dependable and repeatedly manufacturable bus bar termination which avoids the creation of hot spots at the ends of bus bars 15.

Figure 2C:
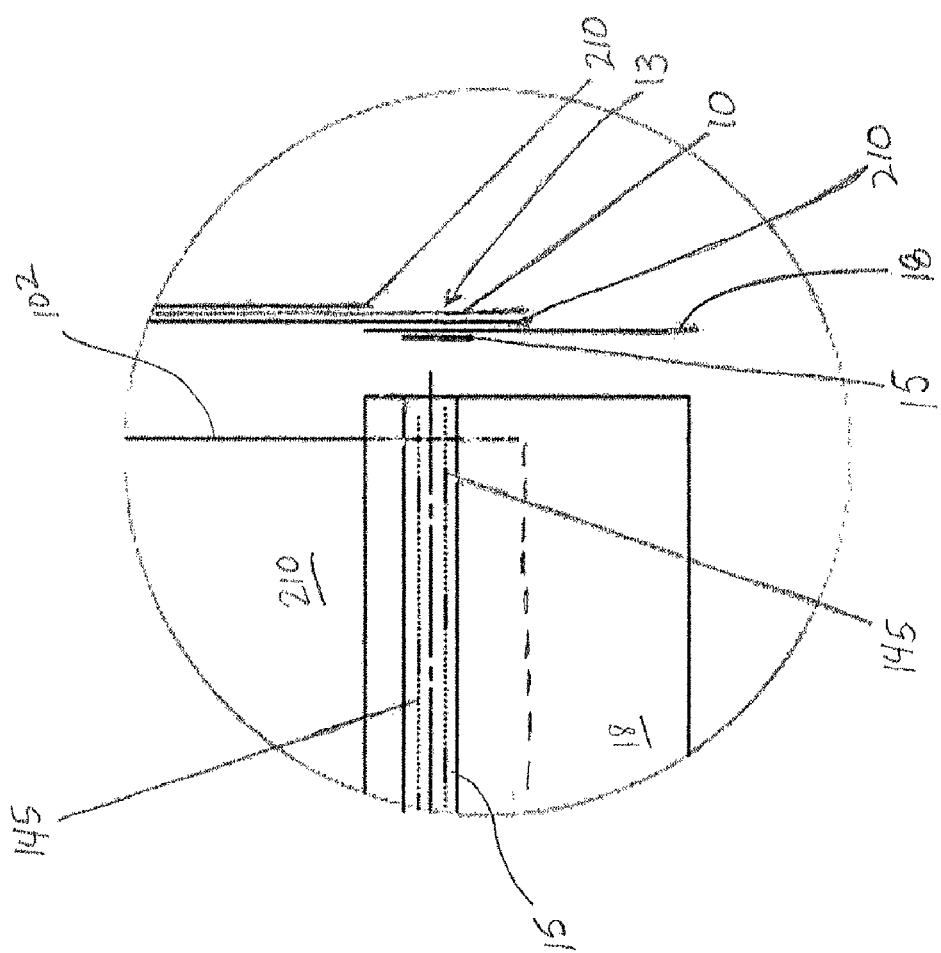
FIG. 2C is an enlarged plan view and corresponding end view schematic of a portion of the assembly shown in FIG. 2A, according to some embodiments of the present invention.
Figure 3A:
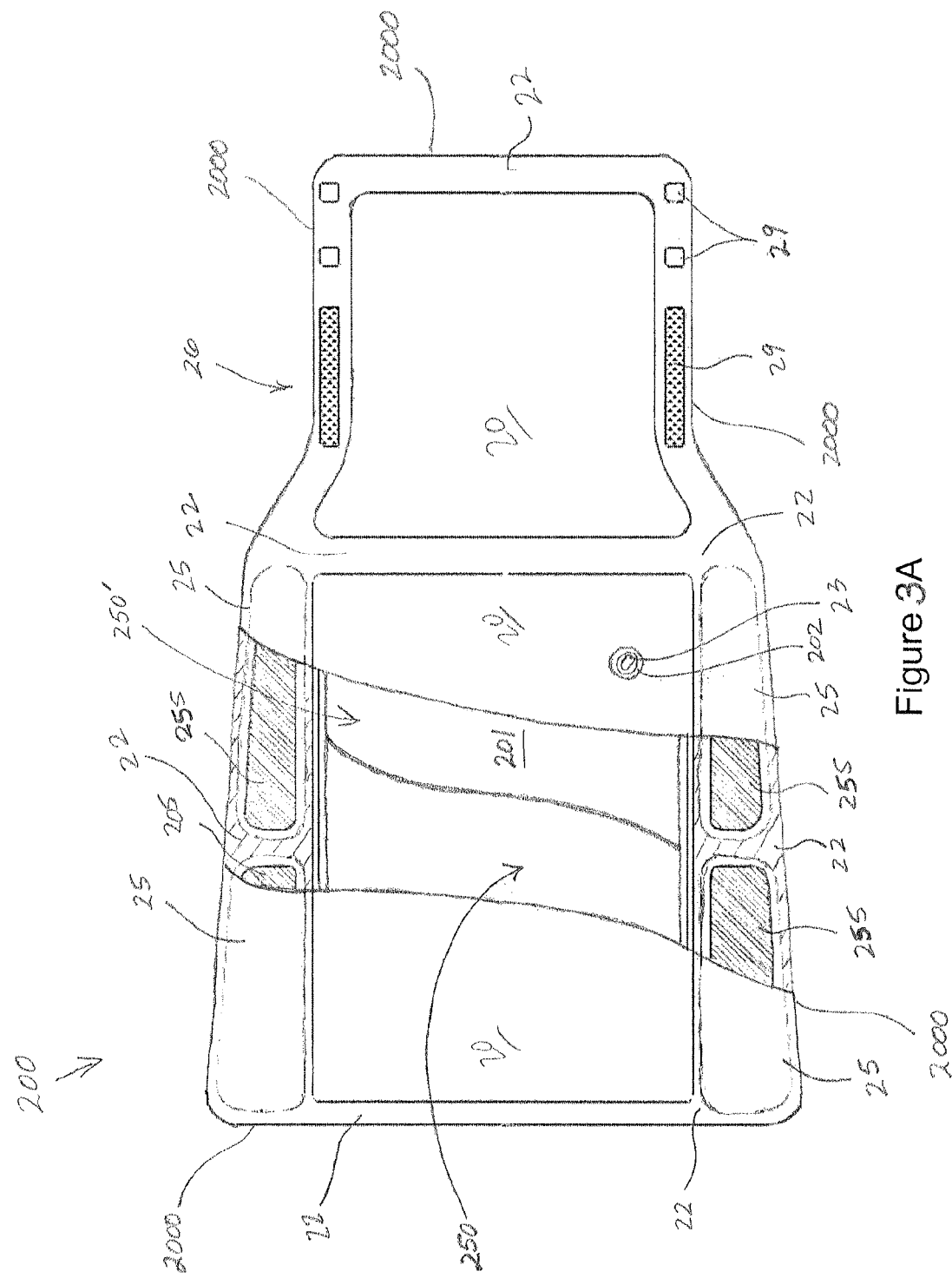
FIG. 3A is a top plan view, including partial cut-away views, of a lower body heating blanket, according to some embodiments of the present invention.

FIG. 2A is a top plan view of a heating element assembly 250, according to some embodiments of the present invention, which may be incorporated by blanket 200, which is shown in FIG. 3A and further described below. FIG. 2B is a section view through section line A-A of FIG. 2A. FIGS. 2A-B illustrate a temperature sensor assembly 421 assembled on side 14 of heating element and heating element 10 overlaid on both sides 13, 14 with an electrically insulating layer 210, preferably formed of a flexible non-woven high loft fibrous material, for example, 1.5 OSY (ounces per square yard) nylon, which is preferably laminated to sides 13, 14 with a hotmelt laminating adhesive. In some embodiments, the adhesive is applied over the entire interfaces between layer 210 and heating element 10. Other examples of suitable materials for layer 210 include, without limitation, polymeric foam, a woven fabric, and a relatively thin plastic film. According to preferred embodiments, overlaid layers 210, without compromising the flexibility of heating assembly 250, prevent electrical shorting of one portion of heating element 10 with another portion of heating element 10 if heating element 10 is folded over onto itself. Because, according to preferred embodiments, heating element assembly 250 will be enclosed within a relatively durable and waterproof shell, for example shell 20 shown with dashed lines in FIG. 2B, and will be powered by a relatively low voltage (approximately 48V). Layers 210 may even be porous in nature to further maintain the desired flexibility of assembly 250.

FIG. 2C is an enlarged plan view and a corresponding end view schematic showing some details of the corner of assembly 250 that is circled in FIG. 2A, according to some embodiments. FIG. 2C is representative of each corner of assembly 250. FIG. 2C illustrates insulating layer 210 disposed over side 14 of heater 10 and extending beneath bus bar 15, optional electrical insulating member 18, and layer 210 disposed over side 13 of heater 10 and terminated adjacent bus bar 15 within lateral portion 12 so that threads of conductive stitching 145 securing bus bars 15 to heater 10 electrically contact heating element 10 along side 13 of heater 10. FIG. 2C further illustrates two rows of conductive stitching 145 coupling bus bar 15 to heater 10, and bus bar 15 and insulating member 18 extending past end 102; a backtack securing stitching 145 may be approximately 0.375 inches long and also extends beyond end 102.

Figure 2D:
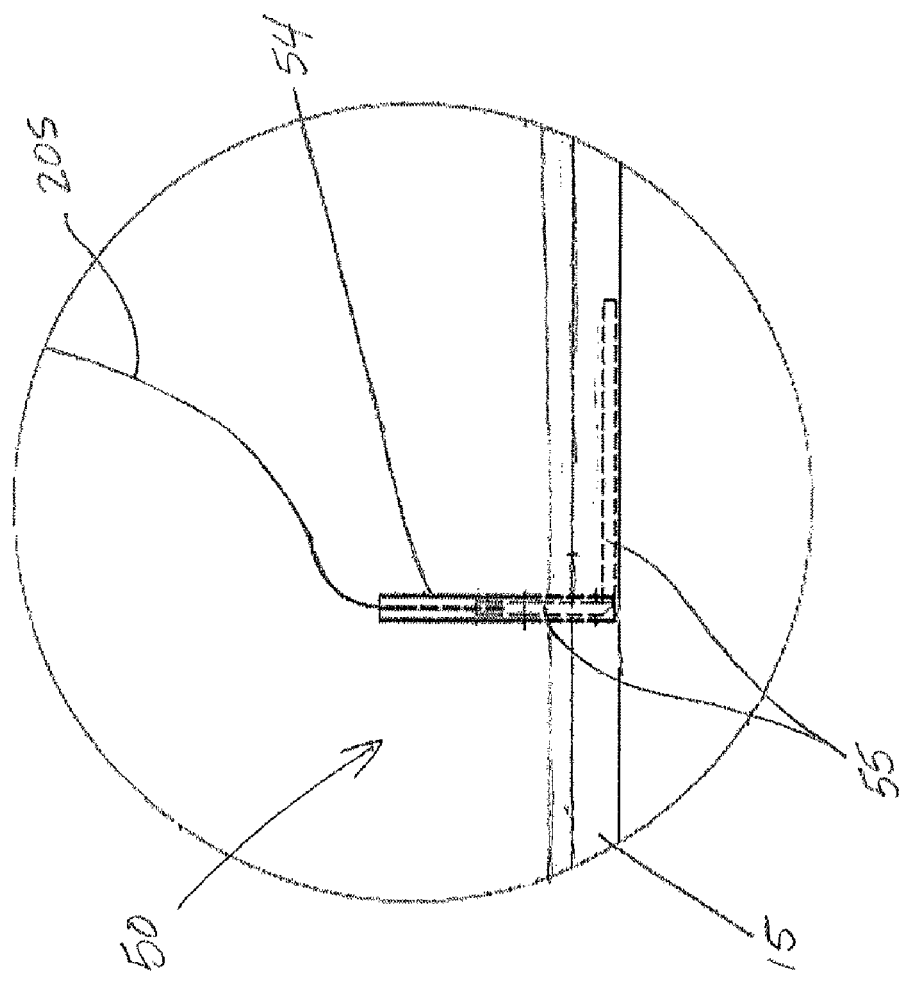
FIG. 2D is an enlarged view of a portion of the assembly shown in FIG. 2A, according to some embodiments of the present invention.
Figure 3B:
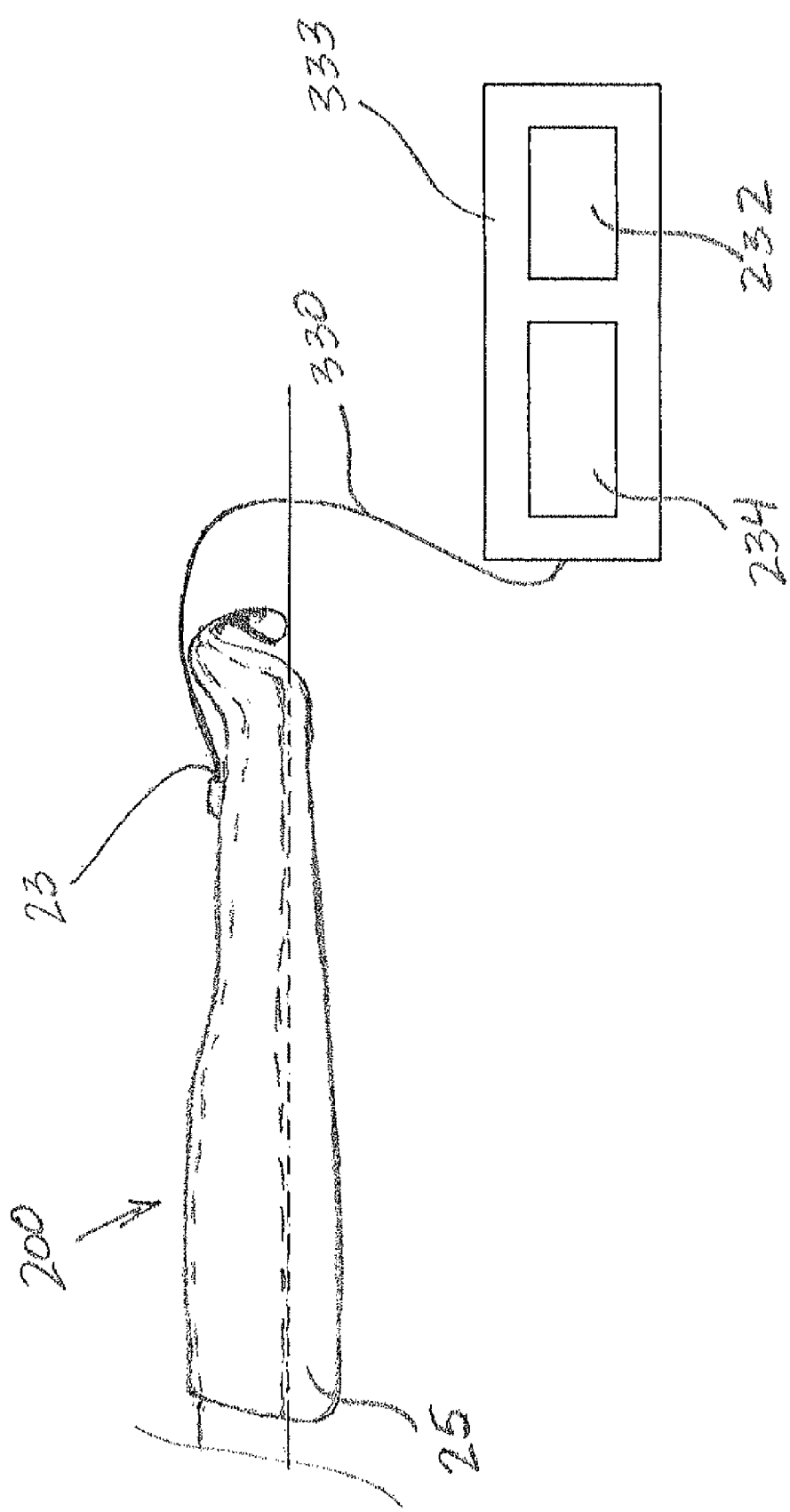
FIG. 3B is a schematic side view of the blanket of FIG. 3A draped over a lower body portion of a patient.

FIG. 2A further illustrates junctions 50 coupling leads 205 to each bus bar 15, and another lead 221 coupled to and extending from temperature sensor assembly 421; each of leads 205, 221 extend over insulating layer 210 and into an electrical connector housing 225 containing a connector 23, which will be described in greater detail below, in conjunction with FIGS. 3A-C. FIG. 2D is an enlarged view of junction 50, which is circled in FIG. 2A, according to some embodiments of the present invention. FIG. 2D illustrates junction 50 including a conductive insert 55 which has been secured to bus bar 15, for example, by inserting insert 55 through a side wall of bus bar 15 and into an inner diameter thereof, the bus bar 15 of the illustrated embodiment being formed by a braided wire tube so that an opening between the wires may be formed for access to the inner diameter. Insert 55 may be secured to bus bar 15 by compressing tubular bus bar 15 around insert 55 and further by stitching 145 that couples bus bar 15 to heating element 10. FIG. 2D further illustrates lead 205 coupled to insert 55, for example, via soldering, and an insulating tube and strain relief 54, for example, a polymer shrink tube, surrounding the coupling between lead 205 and insert 55.

Returning now to FIG. 2B, temperature sensor assembly 421 will be described in greater detail. FIG. 2B illustrates assembly 421 including a substrate 211, for example, of polyimide (Kapton), on which a temperature sensor 21, for example, a surface mount chip thermistor (such as a Panasonic ERT-J1VG103FA: 10K, 1% chip thermistor), is mounted; a heat spreader 212, for example, a copper or aluminum foil, is mounted to an opposite side of substrate 211, for example, being bonded with a pressure sensitive adhesive; substrate 211 is relatively thin, for example about 0.0005 inch thick, so that heat transfer between heat spreader 212 and sensor is not significantly impeded. Temperature sensor assembly 421 may be bonded to layer 210 with an adhesive layer 213, for example, hotmelt EVA. Although not shown, it should be noted that sensor assembly 421 may be potted with a flexible electrically insulating material, such as silicon or polyurethane. Heat spreader 212 is a desirable component of a temperature sensor assembly, according to some embodiments of the present invention, since conductive fabrics employed by heating element 10, such as those previously described, may not exhibit uniform resistance across surface areas thereof.

FIG. 3A is a top plan view, including partial cut-away views, of a lower body heating blanket 200, according to some embodiments of the present invention, which may be used to keep a patient warm during surgery. FIG. 3A illustrates blanket 200 including heating element assembly 250 covered by flexible shell 20; shell 20 protects and isolates assembly 250 from an external environment of blanket 200 and may further protect a patient disposed beneath blanket 200 from electrical shock hazards. According to preferred embodiments of the present invention, shell 20 is waterproof to prevent fluids, for example, bodily fluids, IV fluids, or cleaning fluids, from contacting assembly 250, and may further include an anti-microbial element, for example, being a SILVERion™ antimicrobial fabric available from Domestic Fabrics Corporation. According to the illustrated embodiment, blanket 200 further includes a layer of thermal insulation 201 extending over a top side (corresponding to side 14 of heating element 10) of assembly 250; layer 201 may or may not be bonded to a surface of assembly 250. Layer 201 may serve to prevent heat loss away from a body disposed on the opposite side of blanket 200, particularly if a heat sink comes into contact with the top side of blanket 200. FIG. 3C illustrates insulation 201 extending over an entire surface of side 14 of heating element 10 and over sensor assembly 421. According to the illustrated embodiment, layer 201 is secured to heating element assembly 250 to form an assembly 250', as will be described in greater detail below. According to an exemplary embodiment of the present invention, insulating layer 201 comprises a polymer foam, for example, a 1 pound density 30 ILD urethane foam, which has a thickness between approximately $\frac{1}{8}^{th}$ inch and approximately $\frac{3}{4}^{th}$ inch.

FIG. 3A further illustrates shell 20 forming flaps 25 extending laterally from either side of assembly 250 and a foot drape 26 extending longitudinally from assembly 250. FIG. 3B is a schematic side view of blanket 200 draped over a lower body portion of a patient. With reference to FIG. 3B it may be appreciated that flaps 25, extending down on either side of the patient, and foot drape 26, being folded under and secured by reversible fasteners 29 (FIG. 3A) to form a pocket about the feet of the patient, together effectively enclose the lower body portion of the patient to prevent heat loss. With further reference to FIG. 3B, it may also be appreciated that neither shell 20 nor insulation layer 201 add appreciable stiffness to heating element 10 so that blanket 200 conforms nicely to the contour of the patient's lower body. With reference to FIG. 2A, in conjunction with FIG. 3B, it may be appreciated that temperature sensor assembly 421 is located on assembly 250 so that, when blanket 200 including assembly 250 is draped over the lower body of the patient, the area of heating element 10 surrounding sensor assembly 421 will be in conductive contact with one of the legs of the patient in order to maintain a safe temperature distribution across element 10.

According to some embodiments of the present invention, shell 20 includes top and bottom sheets extending over either side of assembly 250; the two sheets of shell 20 are coupled together along a seal zone 22 (shown with cross-hatching in the cut-away portion of FIG. 3A) that extends about a perimeter edge 2000 of blanket 200, and within perimeter edge 2000 to form zones, or pockets, where a gap exists between the two sheets. According to an exemplary embodiment of the present invention, shell 20 comprises a nylon fabric having an overlay of polyurethane coating to provide waterproofing; the coating is on at least an inner surface of each of the two sheets, further facilitating a heat seal between the two sheets, for example, along seal zone 22, according to preferred embodiments. It should be noted that, according to alternate embodiments of the present invention, a covering for heating assemblies, such as heating assembly 250, may be removable and, thus, include a reversible closure facilitating removal of a heating assembly therefrom and insertion of the same or another heating assembly therein.

FIG. 3C is a top plan view, including partial cut-away views, of heating element assembly 250', which may be incorporated in blanket 200; and FIG. 3D is a cross-section view through section line D-D of FIG. 3C. FIGS. 3C-D illustrates heating element assembly 250' including heating element 10 overlaid with electrical insulation 210 on both sides 13, 14 and thermal insulation layer 201 extending over the top side 14 thereof (dashed lines show leads and sensor assembly beneath layer 201). According to the illustrated embodiment, layer 201 is inserted beneath a portion of each insulating member 18, each which has been folded over the respective bus bar 15, for example as illustrated by arrow B in FIG. 1C, and then held in place by a respective row of non-conductive stitching 345 that extends through member 18, layer 201 and heating element 10. Although layer 210 is shown extending beneath layer 201 on side 14 of heating element, according to alternate embodiments, layer 201 independently performs as a thermal and electrical insulation so that layer 210 is not required on side 14 of heating element 10. FIG. 3C further illustrates, with longitudinally extending dashed lines, a plurality of optional slits in layer 201, which may extend partially or completely through layer 201, in order to increase the flexibility of assembly 250'. Such slits are desirable if a thickness of layer 201 is such that it prevents blanket 200 from draping effectively about a patient; the optional slits are preferably formed, for example, extending only partially through layer 201 starting from an upper surface thereof, to allow bending of blanket 200 about a patient and to prevent bending of blanket 200 in the opposition direction.

Returning now to FIG. 2A, to be referenced in conjunction with FIGS. 3A-C, connector housing 225 and connector 23 will be described in greater detail. According to certain embodiments, housing 225 is an injection molded thermoplastic, for example, PVC, and may be coupled to assembly 250 by being stitched into place, over insulating layer 210. FIG. 2A shows housing 225 including a flange 253 through which such stitching can extend. With reference to FIGS. 3A-B, it can be seen that connector 23 protrudes from shell 20 of blanket 200 so that an extension cable 330 may couple bus bars 15 to a power source 234, and temperature sensor assembly 421 to a temperature controller 232, both shown incorporated into a console 333. In certain embodiments, power source 234 supplies a pulse-width-modulated voltage to bus bars 15. The controller 232 may function to interrupt such power supply (e.g., in an over-temperature condition) or to modify the duty cycle to control the heating element temperature.

FIGS. 3C-D further illustrate a pair of securing strips 217, each extending laterally from and alongside respective lateral portions 11, 12 of heating element 10 and each coupled to side 13 of heating element 10 by the respective row of stitching 345. Another pair of securing strips 271 is shown in FIG. 3C, each strip 271 extending longitudinally from and alongside respective ends 101, 102 of heating element 10 and being coupled thereto by a respective row of non-conductive stitching 354. Strips 271 may extend over layer 201 or beneath heating element 10. Strips 217 preferably extend over conductive stitching 145 on side 13 of heating element 10, as shown, to provide a layer of insulation that can prevent shorting between portions of side 13 of heating element 10 if element 10 were to fold over on itself along rows of conductive stitching 145 that couple bus bars 15 to heating element 10; however, strips 217 may alternately extend over insulating member 18 on the opposite side of heating element 10.

Figure 4A:
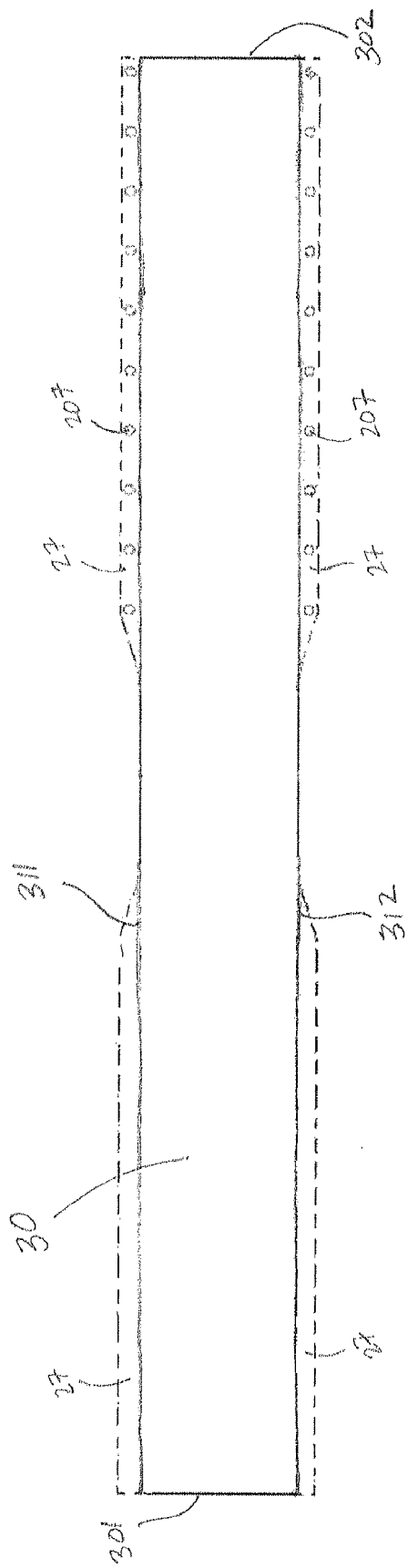
FIG. 4A is a plan view of flexible heating element, according to some alternate embodiments of the present invention.

FIG. 4A is a plan view of flexible heating element 30, according to some alternate embodiments of the present invention. Heating element 30 is similar in nature to previously described embodiments of heating element 10, being comprised for a substantially uniform watt density output, preferably less than approximately 0.5 watts/sq. inch. While a shape of the surface area of heating element 10 is suited for a lower body blanket, such as blanket 200, that would cover a lower abdomen and legs of a patient (FIG. 3B) undergoing upper body surgery, the shape of a surface area of heating element 30 is suited for an upper body heating blanket, for example, blanket 300 shown in FIG. 4C, that would cover outstretched arms and a chest area of a patient undergoing lower body surgery (FIG. 4D).

Figure 4B:
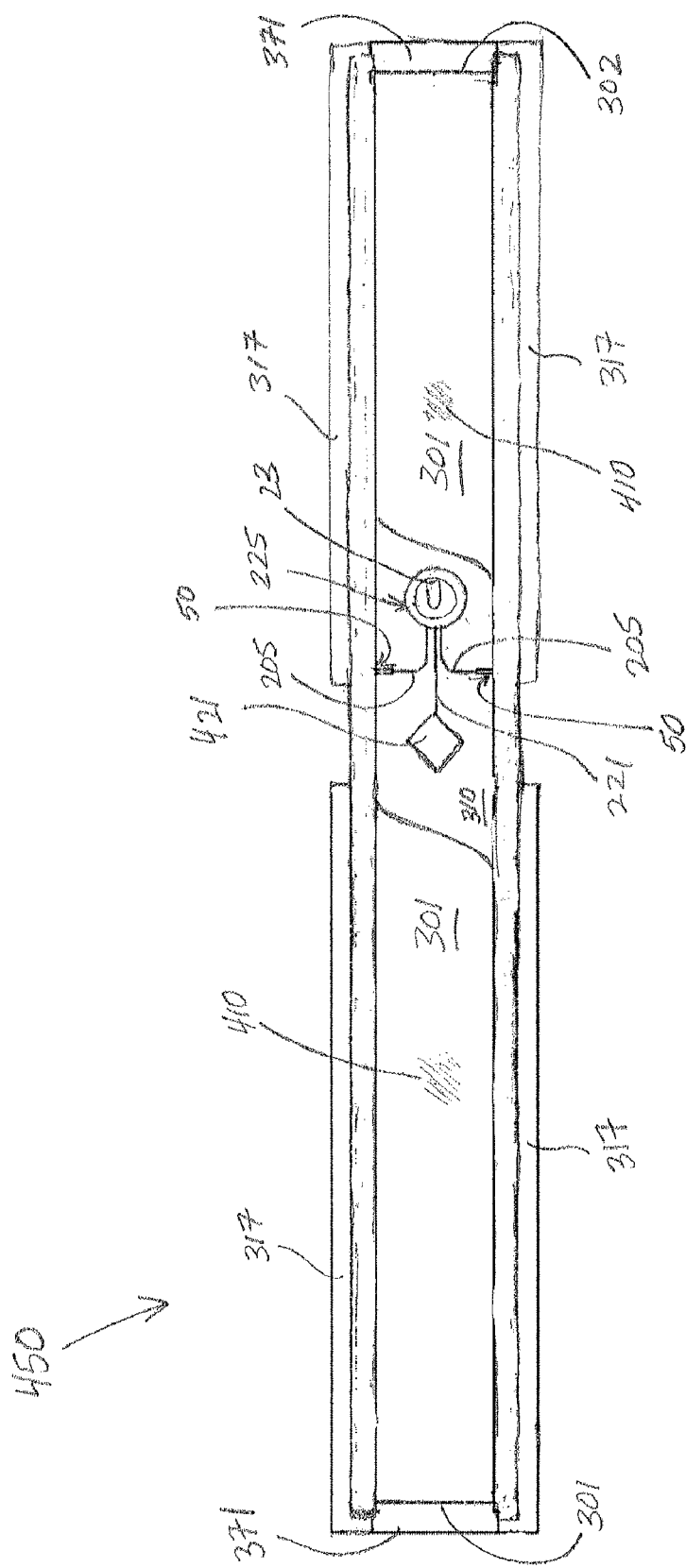
FIG. 4B is a top plan view, including a partial cut-away view, of a heating element assembly, according to some embodiments of the present invention, which may be incorporated in the blanket shown in FIG. 4C.
Figure 4C:
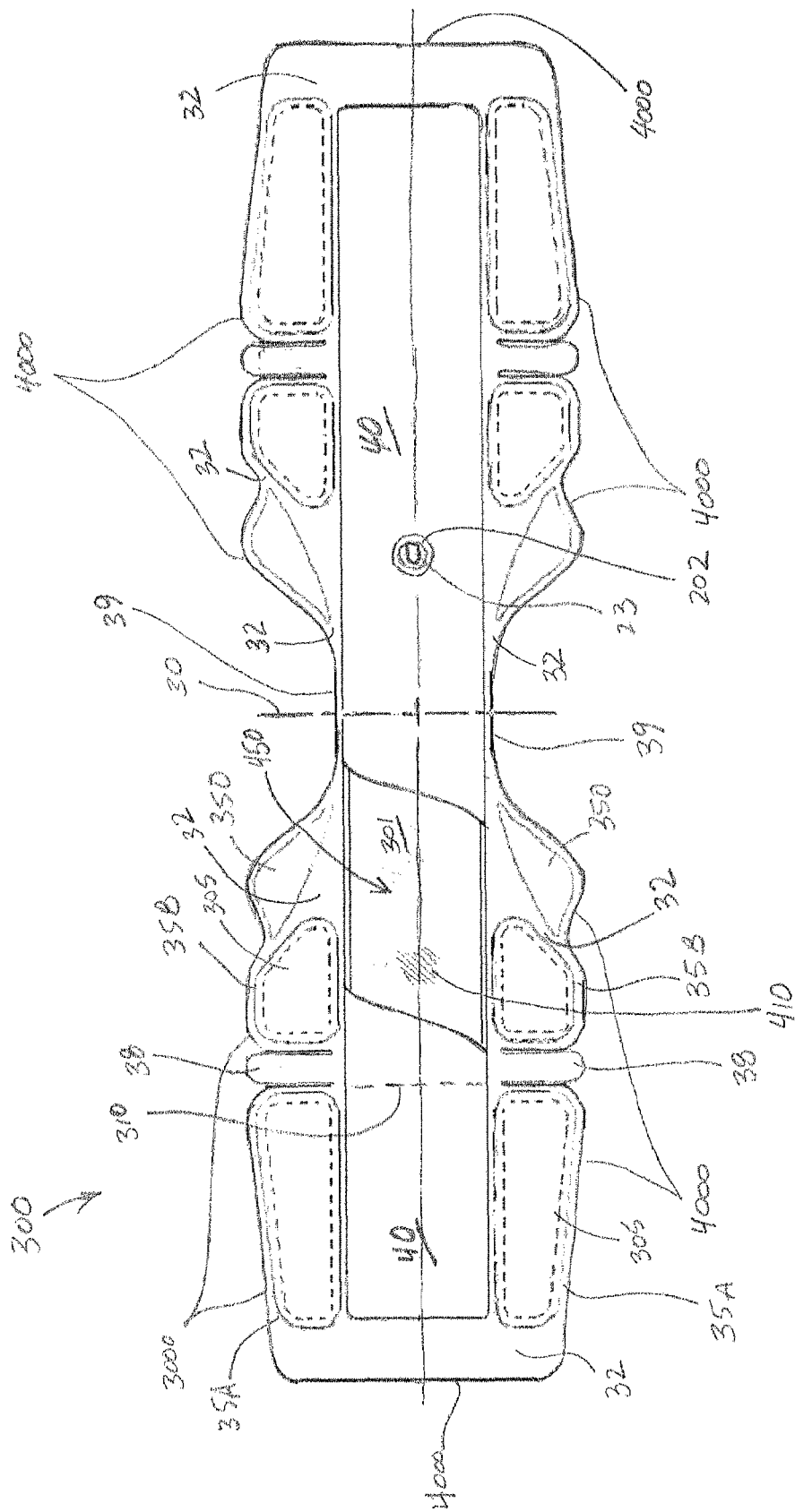
FIG. 4C is a top plan view, including a partial cut-away view, of an upper body heating blanket, according to some embodiments of the present invention.

FIG. 4B is a top plan view, including partial cut-away views, of heating element assembly 450, according to some embodiments of the present invention, which may be incorporated in blanket 300 shown in FIG. 4C. FIG. 4B illustrates assembly 450 having a configuration similar to that of assembly 250', which is illustrated in FIGS. 3C-D. According to the embodiment illustrated in FIG. 4B, temperature sensor assembly 421 is coupled to heating element 30 at a location where element 30, when incorporated in an upper body heating blanket, for example, blanket 300, would come into conductive contact with the chest of a patient, for example as illustrated in FIG. 4D, in order to maintain a safe temperature distribution across element 30; bus bar junctions 50 and connector housing 225 are located in proximity to sensor assembly 421 in order to keep a length of leads 205 and 221 to a minimum. With reference back to FIGS. 3C-D, in conjunction with FIG. 4B, an electrical insulating layer 310 of assembly 450 corresponds to insulating layers 210 of assembly 250', a thermal insulating layer 301 of assembly 450 corresponds to layer 201 of assembly 250', and securing strips 317 and 371 of assembly 450 generally correspond to strips 217 and 271, respectively, of assembly 250'.

FIG. 4C is a top plan view, including partial cut-away views, of upper body heating blanket 300, according to some embodiments of the present invention. FIG. 4C illustrates blanket 300 including heating element assembly 450 covered by a flexible shell 40; shell 40 protects and isolates assembly 450 from an external environment of blanket 300 and may further protect a patient disposed beneath blanket 300 from electrical shock hazards. According to preferred embodiments, shell 40 is similar to shell 20 of blanket 200 in that shell 40 is relatively durable and waterproof and may further include an antimicrobial element or layer extending over an exterior surface thereof. According to the illustrated embodiment, shell 40, like shell 20, includes top and bottom sheets; the sheets extend over either side of assembly 450 and are coupled together along a seal zone 32 that extends around a perimeter edge 4000 and within edge 4000 to form various zones, or pockets, where gaps exist between the two sheets. The sheets of shell 40 may be heat sealed together along zone 32, as previously described for the sheets of shell 20. With reference to FIG. 4B, securing strips 317 may be heat sealed between the sheets of shell 40 in corresponding areas of seal zone 32, on either side of a central narrowed portion 39 of blanket 300, in order to secure heating element assembly 450 within the corresponding gap between the two sheets of shell 40. It should be noted that either of blankets 200, 300, according to alternate embodiments of the present invention, may include more than one heating element 10, 30 and more than one assembly 250/250', 450.

Figure 4D:
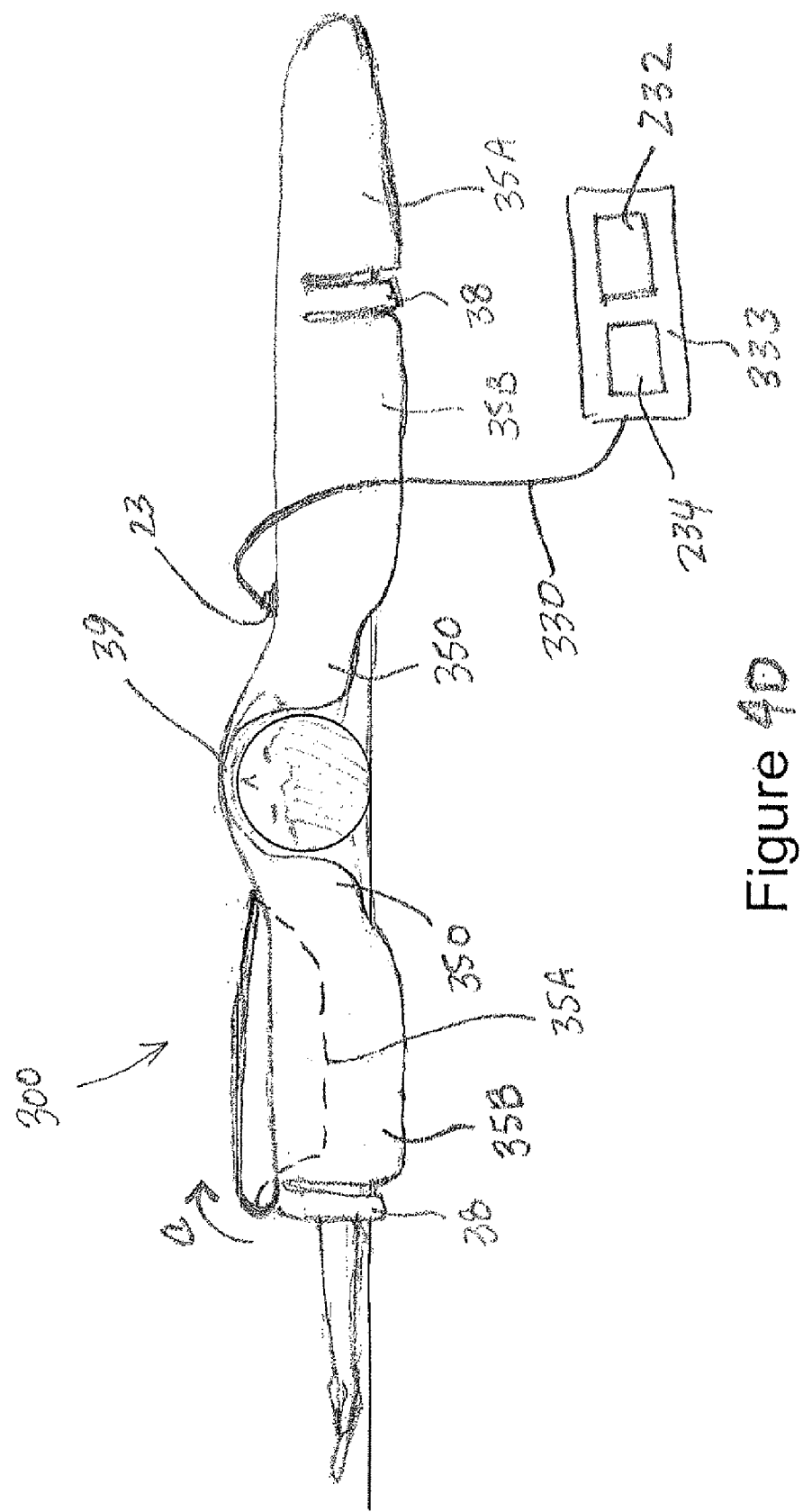
FIG. 4D is a schematic end view of the blanket of FIG. 4B draped over an upper body portion of a patient.

FIG. 4D further illustrates connector cord 330 plugged into connector 23 to couple heating element 30 and temperature sensor assembly 421 of blanket 300 to control console 333.

In the foregoing detailed description, the invention has been described with reference to specific embodiments. However, it may be appreciated that various modifications and changes can be made without departing from the scope of the invention as set forth in the appended claims. Although embodiments of the invention are described in the context of a hospital operating room, it is contemplated that some embodiments of the invention may be used in other environments. Those embodiments of the present invention, which are not intended for use in an operating environment and need not meet stringent FDA requirements for repeated used in an operating environment, need not including particular features described herein, for example, related to precise temperature control. Thus, some of the features of preferred embodiments described herein are not necessarily included in preferred embodiments of the invention which are intended for alternative uses.

The invention claimed is:

1. A flexible heating subassembly, comprising:
   a flexible heater including a first lateral edge, and a second lateral edge opposite the first lateral edge;
   a first conductive bus bar disposed alongside the first lateral edge of the flexible heater;
   a second conductive bus bar disposed alongside the second lateral edge of the flexible heater;
   first and second rows of electrically conductive stitching, the first row of electrically conductive stitching electrically coupling the first conductive bus bar to the flexible heater, the second row of electrically conductive stitching electrically coupling the second conductive bus bar to the flexible heater;
   the first and second conductive bus bars adapted for coupling to a power source for powering the flexible heater;
   a first electrically insulating member interposed between the first conductive bus bar and the flexible heater and being secured therebetween by the first row of electrically conductive stitching, the first electrically insulating member preventing direct electrical contact between the first conductive bus bar and the flexible heater; and
   a second electrically insulating member interposed between the second conductive bus bar and the flexible heater and being secured therebetween by the second row of electrically conductive stitching, the second electrically insulating member preventing direct electrical contact between the first conductive bus bar and the flexible heater.

2. The subassembly of claim 1, wherein the flexible heater comprises carbon.

3. The subassembly of claim 1, wherein the flexible heater comprises a nonconductive layer coated with a conductive material.

4. The subassembly of claim 3, wherein the nonconductive layer of the flexible heater comprises a woven polymer and the conductive material comprises one of: polypyrrole, carbonized ink and metalized ink.

5. The subassembly of claim 3, wherein the nonconductive layer of the flexible heater comprises a non-woven polymer and the conductive material comprises one of: polypyrrole, carbonized ink and metalized ink.

6. The subassembly of claim 3, wherein the non-conductive layer of the flexible heater comprises a non-woven cellulose material and the conductive material comprises one of: polypyrrole, carbonized ink and metalized ink.

7. The subassembly of claim 1, wherein the first and second conductive bus bars comprise a metal wire.

8. The subassembly of claim 7, wherein the metal wire is one of a plurality of braided metal wires.

9. The subassembly of claim 1, wherein the first and second conductive bus bars comprise a metal foil.

10. The subassembly of claim 1, wherein the first and second rows of electrically conductive stitching comprise a non-conductive thread coated with a conductive material.

11. The subassembly of claim 1, wherein the first and second rows of electrically conductive stitching comprise a metal thread.

12. The subassembly of claim 1, wherein each of the first and second electrically insulating members comprise a polymer film.

13. The subassembly of claim 12, wherein the polymer film includes a fibrous material reinforcement.

14. The subassembly of claim 1, wherein each of the first and second electrically insulating members comprise one of: a polymeric material, a cellulose material and a glass fibrous material.

15. The subassembly of claim 1, wherein each of the first and second electrically insulating members comprise a PTFE-coated fiberglass material.

16. The subassembly of claim 1, further comprising a layer of flexible electrical insulation extending over the flexible heater and bonded thereto, the layer extending between each of the first and second electrically insulating members and the flexible heater.

17. The subassembly of claim 1, wherein each of the first and second electrically insulating members include folded-over portions covering respective first and second conductive bus bars.

18. The blanket of claim 1, wherein the first and second rows of electrically conductive stitching pierce through the respective first and second electrically insulating members.

19. The blanket of claim 1, wherein the first and second rows of electrically conductive stitching provide the only electrical coupling between the first conductive bus bar and the flexible heater and between the second conductive bus bar and the flexible heater.

20. The blanket of claim 1, wherein the only electrical coupling between the first conductive bus bar and the flexible heater and between the second conductive bus bar and the flexible heater is provided by electrically conductive stitching.

21. The blanket of claim 1, wherein the first electrically insulating member is interposed between all interfaces of the first conductive bus bar and the flexible heater and the second electrically insulating member is interposed between all interfaces of the second conductive bus bar and the flexible heater.

22. An electric warming blanket, comprising:
a flexible heater including a first lateral edge, and a second lateral edge opposite the first lateral edge;
a first conductive bus bar disposed alongside the first lateral edge of the flexible heater;
a second conductive bus bar disposed alongside the second lateral edge of the flexible heater;
a first row of stitching connecting the first conductive bus bar to the flexible heater;
a second row of stitching connecting the second conductive bus bar to the flexible heater,
the first and second rows of stitching each comprising electrically conductive thread,
the first and second conductive bus bars adapted for coupling to a power source for powering the flexible heater;
a first electrically insulating member interposed between the first conductive bus bar and the flexible heater and being secured therebetween by the first row of stitching, the first electrically insulating member preventing direct electrical contact between the first conductive bus bar and the flexible heater;
a second electrically insulating member interposed between the second conductive bus bar and the flexible heater and being secured therebetween by the second row of stitching, the second electrically insulating member preventing direct electrical contact between the first conductive bus bar and the flexible heater;
a flexible shell enveloping the flexible heater and the first and second conductive bus bars to form a substantially hermetically sealed space for the flexible heater and the conductive bus bars.

23. The blanket of claim 22, wherein the flexible heater comprises carbon.

24. The blanket of claim 22, wherein the flexible heater comprises a nonconductive layer coated with a conductive material.

25. The blanket of claim 24, wherein the nonconductive layer of the flexible heater comprises a woven polymer and the conductive material comprises one of: polypyrrole, carbonized ink and metalized ink.

26. The blanket of claim 24, wherein the nonconductive layer of the flexible heater comprises a non-woven polymer and the conductive material comprises one of: polypyrrole, carbonized ink and metalized ink.

27. The blanket of claim 24, wherein the non-conductive layer of the flexible heater comprises a non-woven cellulose material and the conductive material comprises one of: polypyrrole, carbonized ink and metalized ink.

28. The blanket of claim 22, wherein the first and second conductive bus bars comprise a metal wire.

29. The blanket of claim 28, wherein the metal wire is one of a plurality of braided metal wires.

30. The blanket of claim 22, wherein the first and second conductive bus bars comprise a metal foil.

31. The blanket of claim 22, wherein the conductive thread comprises a non-conductive thread coated with a conductive material.

32. The blanket of claim 22, wherein the conductive thread comprises a metal thread.

33. The blanket of claim 22, wherein each of the first and second electrically insulating members comprise a polymer film.

34. The blanket of claim 33, wherein the polymer film includes a fibrous material reinforcement.

35. The blanket of claim 22, wherein each of the first and second electrically insulating members comprise one of: a polymeric material, a cellulose material and a glass fibrous material.

36. The blanket of claim 22, wherein each of the first and second electrically insulating members comprise a PTFE-coated fiberglass material.

37. The blanket of claim 22, further comprising a layer of flexible electrical insulation extending over the flexible heater and bonded thereto, the layer extending between each of the first and second electrically insulating members and the flexible heater.

38. The blanket of claim 22, wherein each of the first and second electrically insulating members include folded-over portions covering respective first and second conductive bus bars.

39. The blanket of claim 22, wherein the flexible shell comprises upper and lower sheets sealed only about their peripheries to form the substantially hermetically sealed space.

* * * * *